United States Patent [19]

Slocum

[11] Patent Number: 4,762,122

[45] Date of Patent: Aug. 9, 1988

[54] DEVICE AND METHOD FOR PELVIC OSTEOTOMY FIXATION

[76] Inventor: Barclay Slocum, 241 Spy Glass Dr., Eugene, Oreg. 97401

[21] Appl. No.: 11,681

[22] Filed: Feb. 6, 1987

[51] Int. Cl.$^4$ .............................................. A61F 5/04
[52] U.S. Cl. ........................ 128/92 YP; 128/92 VV; 623/22
[58] Field of Search ........ 128/92 YP, 92 YL, 92 YM, 128/92 YJ, 92 V, 92 VY, 92 VV, 92 R, 69; 633/16–18, 22

[56] References Cited

U.S. PATENT DOCUMENTS

| | | | |
|---|---|---|---|
| Re. 28,841 | 6/1976 | Allgower et al. | 128/92 YP |
| 3,824,995 | 2/1974 | Getscher et al. | 128/92 YP |
| 4,120,298 | 10/1978 | Fixel | 128/92 YP |
| 4,479,491 | 10/1984 | Martin | 128/92 YP X |
| 4,545,876 | 6/1984 | Mears | 128/92 YP |

FOREIGN PATENT DOCUMENTS 0100114  2/1984  European Pat. Off. ........ 128/92 YP

OTHER PUBLICATIONS

2453 Hip Arthrodesis Plate, Product Encyclopedia (catalog) Zimmer-USA, Inc., p. B168, 1978.

Primary Examiner—Ronald L. Frinks
Attorney, Agent, or Firm—Kolisch, Hartwell & Dickinson

[57] ABSTRACT

A device and a method related to performing a pelvic osteotomy. A fixation bracket including dual planar plate members joined rigidly at their marginal edges by a web member makes possible the fixation of ilial sections in a desired angular and positional relationship. Elongate holes in each plate member include beveled features that allow the bracket, when secured by screws, compressibly to urge the two ilium sections toward one another normal to the plane of a cut therebetween. In a modification, the angle formed by the web member between the two plate members is adjustable by a surgeon in a range around its nominal value. The improved osteotomy method made possible by the fixation bracket includes offsetting of the ilial section away from the pelvic canal, before its rotated rejoining with the pelvis from which it was separated.

17 Claims, 2 Drawing Sheets

DEVICE AND METHOD FOR PELVIC OSTEOTOMY FIXATION

BACKGROUND AND SUMMARY OF THE INVENTION

This invention relates generally to improved osteotomy fixation, and more particularly to a unique fixation bracket, and a method for using it in a pelvic ostectomy. A preferred manner of practicing the invention is described in conjunction with veterinary surgery on a canine pelvis.

Hip dysplasia is a painful and frequently disabling condition of instability between the acetabulum and the femoral head. It usually results from insufficient formation of the acetabulum, which is the cup-shaped socket that receives the femoral head. As the hip is a load-bearing joint, instability in the positional relationship of the acetabulum and femoral head frequently results in further injury to surrounding tissue.

Surgical techniques for correcting hip dysplasia have been suggested, notably the pelvic osteotomy. In that procedure, an acetabular segment is rotated to allow the underformed acetabulum better to "cover" the femoral head. Fixation plates are frequently used to fix the angular position of the rotated acetabular segment relative to the pelvis. Unfortunately, numerous complications arise as a result of this popular procedure, primarily due to loss of fixation and pelvic canal constriction. The more prevalent loss of fixation problem may leave the patient in worse condition than before the surgery, as the pelvic osteotomy is an invasive procedure requiring three pelvic incisions, the removal of one pelvic section and the separation and rotation of another. The chronic bowel and urinary tract problems that result from constriction of the pelvic canal are, at best, uncomfortable and, at worst, injurious. When coupled with the neuroses that frequently accompany such invasive surgical techniques, these complications render the procedure, as it is conventionally practiced, seriously flawed.

Alternatives to the practice of pelvic osteotomies to correct hip dysplasia have been proposed. Notably, a less invasive osteotomy that lengthens (and optionally torses) the biomechanical femoral neck will, in many cases, correct hip dysplasia without resort to a pelvic osteotomy. It has also been discovered that improved results obtain from a pelvic osteotomy when it is performed in combination with such a femoral neck-lengthening osteotomy. Such a method is described in my co-pending application, Ser. No. 06/946,863, filed Dec. 29, 1986, for "Osteotomy Method for Biomechanical Femoral Neck-Lengthening and Torsion." Nevertheless, there will be circumstances that demand the continued use of the pelvic osteotomy procedure.

Loss of fixation results from the use of narrow fixation plates that, when subjected to the shear and torque forces incident to acetabular segment rotation, tend to fracture, bend or loosen. The failure of fixation plates to counteract these torsional forces permits loss of fixation and uncontrolled rotation of the acetabular segment, and retards the bone healing process. A fixation device that eliminated these fixations problems would significantly improve the prospects for a successful pelvic osteotomy.

Constriction of the pelvic canal results from rotation of the acetabular segment. When the acetabular segment is rotated on its median axis, the depending portions thereof move medially in the direction of the opposite ilium. Depending upon the degree of rotation, the resulting constriction of the pelvic canal ranges from negligible to occlusive. Even when appreciated, the problem of pelvic canal restriction has heretofore been unavoidable because conventional fixation plates do not allow for the securing of bone sections that are offset from one another. A fixation bracket and improved procedure that allow both rotation and offsetting of the acetabular segment relative to the pelvis would permit stabilization of the coxofemoral joint without the problematic restriction of the pelvic canal.

The present invention discloses a fixation bracket and an improved pelvic osteotomy technique by which both the loss of fixation and canal constriction problems may be avoided.

A principal object of the invention is to provide a fixation bracket that is not subject to fracturing, bending or loosening when used in a pelvic osteotomy procedure.

Another important object of the invention is to provide a fixation bracket, the installation of which permits the securing of a rotated acetabular segment to the pelvis under axial compression.

A further object of the invention is to provide a bracket of the type outlined that is easily adaptable to a range of acetabular segment rotation requirements.

According to a preferred embodiment of the invention, a fixation bracket is described that includes a pair of generally planar fixation plates joined rigidly at their marginal edges in predetermined relative-angular and -positional relationship. Each plate is intended for securement by screws to one of the to-be-joined pelvic sections, which consist of a cut, rotated and offset acetabular segment and the ilium section from which it has been separated. The angle between the planes of the fixation plates is fixed such that median axes of the plates are offset (laterally) from one another. This offset provides the necessary compensation for the rotation that would otherwise result in the constriction of the pelvic canal. The stair-stepped offset between the plates relative to the line of intersection of their planes serves the purpose of generally conforming the bracket to the ilium's natural incline in order to maximize securement thereto (and to the sacrum, if desired).

In its preferred embodiment, the fixation bracket takes the form of opposite, stair-step-shaped plates, having parallel surfaces, joined at their marginal edges by a normally disposed, planar web of similar thickness, also having generally parallel surfaces. Each plate has three elongate holes, approximately equally spaced across the two-dimensional expanse of the plate. The long axis of the elongate holes is perpendicular to the plates' joined marginal edges. In an area at the end of each hole nearer the web, the plates are beveled to provide an inclined surface. When securing screws are tightened, these inclined surfaces provide, by wedging action against the underside of the screws' heads, relative movement between the bracket and the two ilium sections to which it is being secured, thereby urging the ilium sections toward each other normal to the plane of the cut.

In a modification to the preferred embodiment of the invention, a fixation bracket is described in which the web member takes the form of an isthmus. The isthmus is made with a sufficiently small cross section that it may be altered (pre- or intra-operatively) to adjust the angle between the two plates.

According to the preferred method of practicing the invention, an acetabular segment is both rotated and offset to increase the effective width of the pelvic canal. The method principally involves (1) removing the pubic ramus from the pelvis, (2) cutting through the tuber ischii parallel with the sagittal plane, (3) cutting through the ilium in the transverse plane just caudal to the sacro-iliac joint, (4) rotating the thus created, free ilium section on its median axis, (5) offsetting the section relative to the pelvis and (6) fixing the sections (using the fixation bracket described herein).

Fixation of the remaining free end of the rotated and offset ilium section is, in the preferred method, accomplished by conventional wiring. Fixation will be understood to include bone-grafting around the area of the second cut, as by use of the pubic ramus previously removed, to promote osteosynthesis.

Use of the preferred embodiment of (or the modification to) the device of this invention, in conjunction with the improved osteotomy method that includes offsetting of the acetabular segment before fixing it, enables the practice of a pelvic osteotomy without the complications described above. In particular, loss of fixation and pelvic canal restriction may be prevented, enabling the successful stabilization of the coxofemoral joint.

These and other advantages and features of the invention will be come more fully apparent when the detailed description below is read with reference to the accompanying drawings.

DESCRIPTION OF THE DRAWINGS

In the interest of clarity, it will be appreciated that the preferred embodiment of the improved device of, and the preferred method of practicing, the invention are illustrated and described consistently, with respect to orientation. Thus, the orientation of the brackets illustrated in FIGS. 1 through 7 is described using anatomical terminology, as though the brackets were positioned on the patient's pelvis and viewed laterally therefrom.

DETAILED DESCRIPTION OF THE INVENTION

Figure 1:
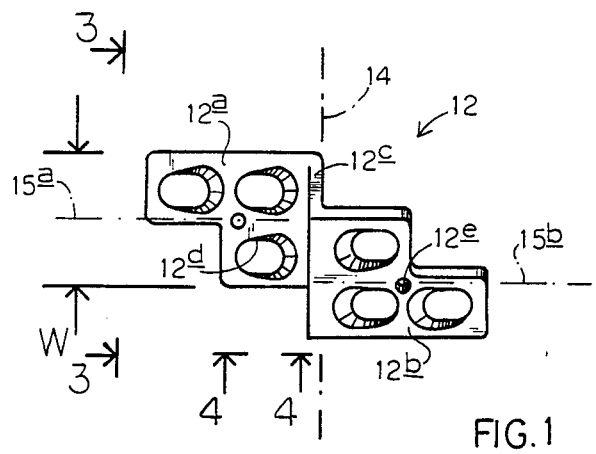
FIG. 1 is a lateral view of the left fixation bracket proposed by the present invention.
Figure 2:
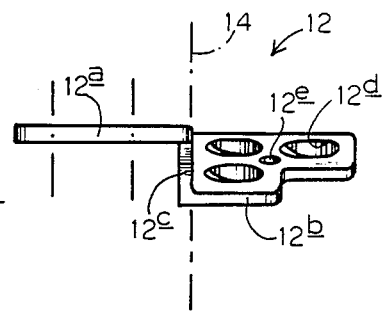
FIG. 2 is a dorsal view of the bracket of FIG. 1 (taken from the top side of FIG. 1).
Figure 3:
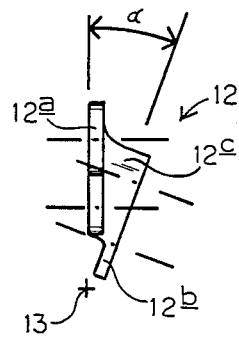
FIG. 3 is a cranial view of the same fixation bracket taken generally along line 3—3 in FIG. 1.

Referring collectively to FIGS. 1 through 3, the fixation bracket proposed by the present invention, and depicted in orthogonal views of its preferred embodiment, is indicated at 12. In this bracket, two generally planar, stair-stepped fixation plates, or plate expanses, 12a, 12b are joined at their near marginal edges by a web 12c which lies, as will become more fully apparent below, in a plane 14 that generally coincides with the plane of a cut that is made during practice of the method of the invention. Each plate includes means, such as holes 12d, 12e, for promoting securement to an ilial section. Although it has been found that three holes such as 12d per plate provide adequate securement of to-be-joined ilial sections, it will be appreciated that the number and arrangement of the holes may differ from that shown. It will also be appreciated that, although the bracket illustrated herein is intended for use on an afflicted left ilial section, a "mirror-image" bracket may be made, within the spirit of this invention, for use on an afflicted right side of the pelvis.

Importantly, and referring specifically now to FIG. 1, the width W of each plate represents a substantial fraction of the width of the ilial section to be joined as discussed below, thus providing substantial resistance, when secured, to shear and torsional forces incident upon the joined sections.

The fixation bracket of FIG. 1 is shown in a dorsal view in FIG. 2. The resulting view is in the plane of plate 12a, and shows the relative angle and offset of plate 12b. The angle and positioning of the two plates relative to one another is defined by the size and shape of web 12c, which is disposed in generally normal relationship with the plates and rigidly joins them.

Figure 11:
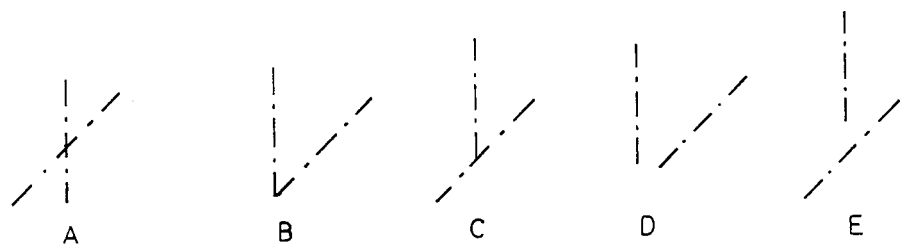
FIG. 11 is a schematic illustration, in a cranial view, of various bracket configurations that may be made in accordance with the invention.

FIG. 3 shows a cranial view of bracket 12, and represents an end view of plate 12a and a planar view of web 12c. This illustration shows most clearly the preferred embodiment's angular and positional relationship between plates whos planes intersect in a line offset from the plates' median lines, or axes, 15a, 15b. FIG. 3 also clearly shows the situation that, in the preferred embodiment now being described, plates 12a, 12b are offset from one another relative to the line 13 of intersection of the planes of these two plates. This preferred plate arrangement forms, in end view, what may be thought of as V-shaped bracket. It will be appreciated that, depending upon the nature and extent of the acetabulofemoral mismatch, the planes in which the plates lie may intersect at or near median axes 15a, 15b to form, in end view, what may be thought of as an X-shaped bracket. Other useful bracket configurations that may be made in accordance with this invention are illustrated in FIG. 11 and will be discussed below. The angle $a$ between the plates is, typically, 20° or 30°, but, in practice, this angle is determined by the amount of rotation needed to enable the acetabulum to "cover" the femoral head. It will be appreciated that a fixation bracket made in accordance with this invention may have any desired angle between the plates.

Figure 4:
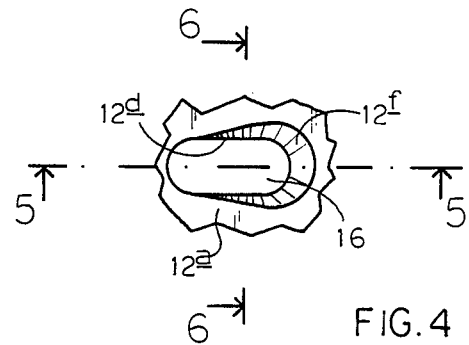
FIG. 4 is a fragmentary lateral view corresponding to FIG. 1, showing a hole in enlarged detail
Figure 5:
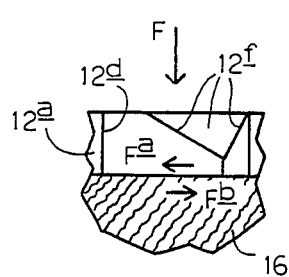
FIG. 5 is a fragmentary cross section taken generally along line 5—5 in FIG. 4.
Figure 6:
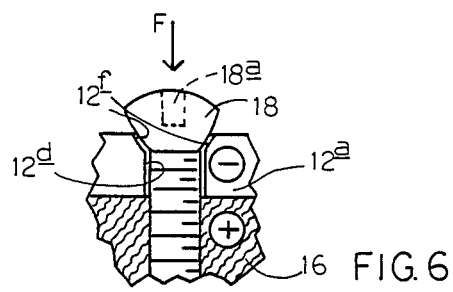
FIG. 6 is a fragmentary cross section taken generally along line 6—6 in FIG. 4, rotated 90° counterclockwise, and further showing a screw extending through the hole.

Turning attention now to FIGS. 4 through 6, details of securement and compression means are shown in the context of the bracket and a to-be-fixed bone section. FIG. 4 is a fragmentary lateral view of the right hole 12d in plate 12a of FIG. 1, with to-be-fixed bone section 16 visible through hole 12d. In the vicinity of one end of hole 12d, the plate is provided with spherical bevel 12f, which presents a differential axial drive clearance for screw 18 (see particularly FIG. 6) extending through hole 12d. As will be further discussed below, this differential structure between the proximal end (that nearer the marginal edge of the plate) and distal end of elongated holes such as 12d provides for urging, into axial compression, the cut surfaces of the bone sections to be fixed.

As shown in FIG. 5, a fragmentary cross section taken along line 5—5 in FIG. 4, a force vector F, incident upon bevel 12f (shown in FIG. 5, for the sake of clarity, without spherical curvature) of plate 12a, will act to wedge plate 12a in the direction indicated by force vector Fa. If section 16 were secured against movement in such direction, as by extending a screw through hole 12d into section 16, this wedging action would promote relative movement between plate 12a and section 16, as indicated by force vectors Fa and Fb.

FIG. 6 illustrates this wedging action by a fragmentary cross section view at a 90° angle to that of FIG. 5. Spherical head screw 18 with hexagonal drive feature 18a is shown extending through hole 12d into section 16. As screw 18 is further tightened, illustrated schematically by force vector F, the tendency, due to the wedging action described above, is that plate 12a will be urged toward the viewer (out of the page) as indicated by $\ominus$, and ilial section 16 will be urged away from the viewer (into the page) as indicated by $\oplus$. Referring back momentarily to FIG. 1, it will be understood that holes such as 12d, with bevels such as 12f, are oriented to afford opposition wedging action between the two plates. Thus, securing each plate to its respective ilial section, as shown in FIG. 6 and discussed below, results in the compressive urging of the ilial sections toward one another, normal to the plane of the ilial cut.

In its preferred embodiment, the bracket of the present invention is a metal casting, although it may be made of any suitably rigid material. The substantial surface area provided in each plate, which, but for the holes, would be approximately the square of its width W, as shown in FIG. 1, provides substantial, planar surface resistance against movement relative to an ilial section. The bracket may be secured to the to-be-fixed ilial sections by forming holes and extending screws therethrough, which, when tightened, enable the bracket to resist shear forces in plane 14 and torsional forces about an axis normal thereto (e.g. axes 15a, 15b). The bracket's unique structure, including dual plates rigidly joined by a web that defines and maintains their relative-angular and -positional relationship, provides for the rigid fixation of two ilial sections that have been rotated and offset. Such offset ensures that, when the acetabular segment is rotated, the effective diameter of the pelvic canal is maintained.

Generally, the more underformed the acetabulum, the greater the rotation required to allow the acetabulum to "cover" the femoral head. The greater the rotation, the greater also the offset needed to prevent constriction of the pelvic canal by depending portions of the rotated acetabular segment. Thus, in a modification to the preferred embodiment of this invention, a fixation plate is described in which the web is isthmus-shaped and dimensioned to allow a range of yieldable adjustability in the angle between the plates, while ensuring that the chosen angle and offset are securely maintained.

Figure 7:
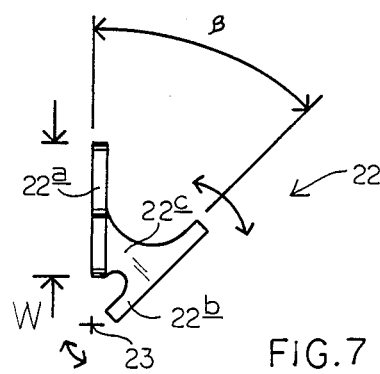
FIG. 7 is a cranial view similar to FIG. 3, showing a modified bracket in which a web joining the plates is isthmusshaped and dimensioned to allow adjustment of the angle between the plates.

In FIG. 7, this modification is shown, in an illustration corresponding to the preferred embodiment shown in FIG. 3. Shown in a cranial view is an adjustable bracket 22. Fixation plates 22a, 22b are rigidly joined by isthmus-shaped web 22c, which is dimensioned controllably to yield to adjustment by the surgeon. Curved arrows indicate the permissible range of resistive, angular adjustment of plate 22a with respect to plate 22b. Nominal angle $\beta$ is, typically, 30° or 45°, and the range of angular adjustment is, typically, ±10°. It will be appreciated that, within the spirit of the present invention, nominal angle $\beta$, as well as the angle of adjustability, may vary from these values, depending upon the severity of the underformation of the acetabulum.

The modified bracket shares all the other features of the bracket of the preferred embodiment, including spherically beveled, elongated holes formed in stair-stepped plates 22a, 22b of width W. Just as was true in the case of bracket 12, in bracket 22, plates 22a, 22b are offset from one another relative to the line 23 of intersection of their planes. Thus, the modification is to the web 22c only, whose size and shape allows a greater range of rotation and offset, and adjustability in the nominal angle between the joined plates. It will be appreciated that yieldable adjustability may be accomplished by other means, so long as the overall rigidity of the fixation bracket is not compromised.

Figure 8:
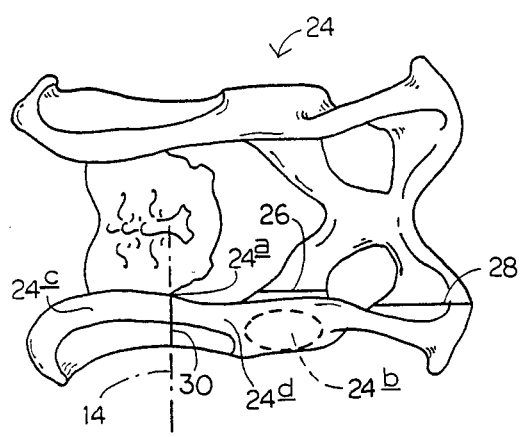
FIG. 8 is a dorsal view of a canine pelvis (removed) showing the location of pelvic osteotomy cuts made according to the improved osteotomy method offered by the invention.
Figure 9:
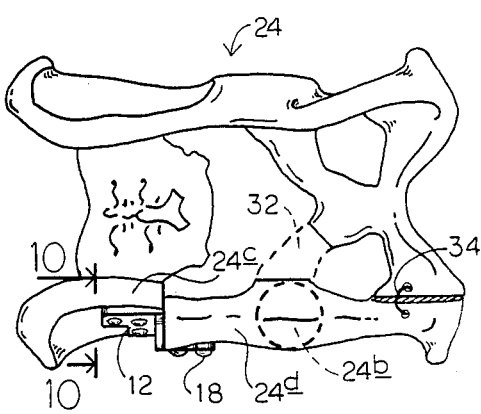
FIG. 9 is similar to FIG. 8, except that it shows the final result of an osteotomy performed by the improved method of the present invention, with the acetabular segment rotated, offset and fixed.
Figure 10:
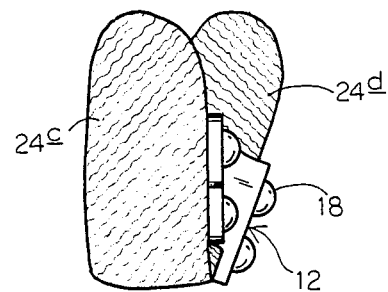
FIG. 10 is a fragmentary cross section taken generally along line 10—10 in FIG. 9, rotated 90° counterclockwise to show, in a cranial view, the cut/rotated/offset ilium sections fixed with a fixation bracket of the preferred embodiment and by the improved method of practicing the invention.

Reference to FIGS. 8 through 10 reveals how the fixation bracket is used in the performance of an improved pelvic osteotomy. FIG. 8 shows a dorsal view of the pelvis (removed), indicated generally at 24. In the preferred practice of the improved method, three planar cuts are made in the afflicted side of the pelvis. Cut 26 is produced, generally parallel with the sagittal plane, in the pubic ramus in order to free a section thereof for removal. Next, cut 28 is produced, generally parallel with the sagittal plane, through the tuber ischii. Finally, cut 30 is produced through the iliam, this cut being oriented generally in the transverse plane, and being located caudal to sacro-iliac joint 24a and cranial to acetabulum 24b. This combination of through cuts creates section 24d that is free from the remainder of the pelvis. This free section may now be rotated relative to the pelvis, about an axis generally parallel with the intersection of the sagittal and frontal planes, to effect rotation and offset relative to ilial section 24c. The result of such rotation is the repositioning of underformed acetabulum 24b better to "cover" the femoral head (not shown). It will be appreciated that, within the spirit of this invention, the improved osteotomy method may be used to correct an afflicted right side of the pelvis as easily as the left.

Reference to FIG. 9 reveals the result of the completed practice of the improved method. Here the free section 24d has been rotated as indicated (clockwise as viewed along line 10-10), and fixed by bracket 12, screws 18 and wire 34. A section of the pubic ramus has been removed, as indicated by dotted lines at 32, to provide some relief for the pelvic canal. Bracket 12 has been secured to pelvis 24 by screws 18, with one plate securing ilial section 24c and the other plate securing cut/separated/rotated/offset ilial section 24d in new relative-angular and -positional relationship. Acetabulum 24b is, by this rotation and offset, both closer to the femoral head and better positioned to receive it. For the purpose of clarity, the important bone-grafting part of the fixing step is not shown.

FIG. 10 shows a fragmentary cross section of the newly positioned ilial sections. Fixation bracket 12 is shown secured to ilial sections 24c, 24d by screws, such as screw 18. As illustrated, and representing an important improvement over conventional osteotomy method and apparatus, the rotation results in no constriction of the pelvic canal. This is because the bracket offsets the free section so that its depending portions, when rotated, do not protrude into the canal. It will be appreciated that the adjustable bracket, described herein as a modification to the preferred embodiment of the invention, would be installed similarly, but would result in a larger nominal rotation and a larger corresponding offset of the free section.

Turning finally to FIG. 11, various bracket configurations, which may be made in accordance with the invention, are schematically illustrated in a cranial view. It will be appreciated that the webs joining the plates of the various configurations have, to promote clarity, been omitted. Illustration A shows a bracket in which the plates generally are disposed, in a cranial view, in the shape of an X. Illustration B shows the V-shaped bracket of the preferred embodiment described herein. Configuration C may be thought of as a Y-shaped bracket in which the line of intersection of the planes in which the plates lie is generally collinear with (rather than merely parallel with) one of the plates' median axes. The plate configuration illustrated at D of FIG. 11 is a modification to that of B, wherein the "V" is disjoint. Configuration E is a modification to that of C, wherein the "Y" is disjoint. It will be appreciated that this set of schematics is illustrative only, and not comprehensive of the myriad bracket configurations that are within the purview of the instant invention.

The advantages offered by this invention should be apparent to those skilled in the art. A pelvic osteotomy performed with the important, additional, offset step will preclude most, if not all, of the postoperative complications that attend the conventional pelvic osteotomy. Loss of fixation due to a fractured, bent or loosened fixation plate is avoided by the integral structure of a bracket having opposite plates of substantial planar expanse and substantial width relative to the ilial sections to be joined, and a rigid, planar web lying in the plane of the cut and joining these plates in predetermined relative-angular and -positional relationship. The further important feature of compression-effecting means for urging the ilial sections toward one another normal to the ilial cut ensures that the joined sections are maintained indefinitely in properly abutted relationship.

Pelvic canal constriction is prevented by the unique structure of both the preferred embodiment and its modification: a fixation bracket that defines, and enables securement of, the desired angular and positional relationship between the to-be-joined ilial sections. By its offset, the fixation bracket of the present invention allows a free ilial section to be rotated and fixed away from, so as to increase the effective width of, the pelvic canal. By the improved pelvic osteotomy procedure of the present invention, and the unique fixation bracket that makes it possible, the acetabulum may be rotated and offset into a position to "cover" the femoral head, thus stabilizing the coxofemoral joint.

Accordingly, while a preferred embodiment of the invention and a modification thereof, as well as a preferred improved method of practicing the invention, have been described herein, it is appreciated that further modifications are possible that come within the scope of the invention.

It is claimed and desired to secure by Letters Patent:

1. In the field of pelvic osteotomy apparatus used to orient two cut and separated ilial sections, a fixation bracket comprising
   means defining a pair of generally planar fixation plate expanses, and
   generally planar web means joining said expanses whereby the same occupy planes intersecting along a line that is generally normal to the plane of said web means.

2. In the field of pelvic osteotomy apparatus used to orient two cut and separated ilial sections, a fixation bracket comprising
   means defining a pair of generally planar fixation plate expanses, and
   generally planar web means joining said expanses whereby the same occupy planes intersecting along a line that is generally normal to the plane of said web means and that is offset from those median axes of said expanses which substantially parallel said line.

3. In the field of pelvic osteotomy apparatus used to orient two cut and separated ilial sections, a fixation bracket comprising
   generally planar web means defining a pair of generally planar fixation plate expanses, and
   means joining said expanses whereby the same occupy planes intersecting along a line that is generally normal to the plane of said web means, with the expanses being offset from one another relative to said line.

4. In the field of pelvic osteotomy apparatus used to orient two cut and separated ilial sections, a fixation bracket comprising
   means defining a pair of generally planar fixation plate expanses, and
   generally planar web means joining said expanses whereby the same occupy planes intersecting along a line that is generally normal to the plane of said web means and that is offset from those median axes of said expanses which substantially parallel said line, and with said expanses offset from one another relative to said line.

5. The bracket of claims 2, 3 or 4, wherein said joining means is yieldably adjustable to alter the angle between such planes.

6. In the field of pelvic osteotomy apparatus used to orient two cut and separated ilial sections, a fixation bracket comprising
   dual fixation plates, each having an inner and an outer surface and a marginal edge adapted to lie generally in the plane of such a cut, each of said plates having a width, measured along an axis parallel with its said marginal edge, which is an appreciable fraction of the width, measured vertically in the vicinity of such cut, of a to-be-associated ilial section, each of said plates being dimensioned to provide a contact surface area with the lateral surface of one such ilial section, such area being generally the square of the plate's width, and each of said plates being intended for securement to one such ilial section, and a web rigidly connecting said marginal edges of said plates and being generally perpendicular to both of said plates, said web being of predetermined size and shape to fix the relative-angular and -positional relationship between the plates.

7. The bracket of claim 6, further including means formed in said plates promoting securement of the latter to such sections.

8. The bracket of claim 7, wherein said promoting means includes compression-effecting means for urging such ilial sections against one another along an axis normal to such a cut during securement of the bracket to the sections.

9. The bracket of claim 7, wherein said promoting means takes the form of plural holes.

10. The bracket of claim 8, wherein said promoting means takes the form, in each plate, of plural elongate holes, each having a long axis generally perpendicular to said marginal edge and having proximal and distal end-configurations together defining said compression-effecting means.

11. The bracket of claim 10 that is usable with a selected fixation screw, wherein, in relation to such screw, the proximal and distal end-configurations offer differential axial drive clearance for the screw, with the proximal end-configuration offering drive clearance which is greater than that offered by the distal end-configuration.

12. The bracket of claims 6, 7, 8 or 9, wherein said relative-angular relationship of said fixation plates is infinitely adjustable within a range of angles including a predetermined nominal angle.

13. The fixation bracket of claim 12, wherein such nominal angle is approximately 30°.

14. The fixation bracket of claim 12, wherein such nominal angle is approximately 45°.

15. In the field of pelvic osteotomy apparatus used to orient two cut and separated ilial sections, a fixation bracket comprising opposing dual plate members each including a marginal edge, with each member having a width, measured along an axis parallel with its said marginal edge, which is an appreciable fraction of the width, measured vertically in the vicinity of such a cut, of a to-be-associated ilial section, each of said members being dimensioned to provide a contact surface area with the lateral surface of one such ilial section, such area being generally the square of the member's width, one of said members being intended for securement to one such ilial section cranial to such a cut, and the other member being intended for securement to the other such ilial section caudal to such a cut, and a web member rigidly joining said plate members adjacent their said marginal edges, said web member being adapted to lie generally in the plane of and adjacent such a cut, and being generally perpendicular to both of said plate members, with the web member being of predetermined size and shape to fix the relative-angular and -positional relationship between the plate members.

16. An improved method of performing a pelvic osteotomy that includes rotation and offset, comprising removing the pubic ramus from the pelvis, producing a first cut through the tuber ischii generally parallel with the sagittal plane, producing a second cut through the ilium generally in the transverse plane, such second cut being located caudal to the sacro-iliac joint and cranial to the acetabulum to create relatively movable ilial sections including a free section bearing the acetabulum, rotating the thus-created free section relative to the other section about an axis which is generally normal to the plane of the second cut, thus producing the desired angular relationship therebetween, offsetting the free section relative to the other section to increase the effective width of the pelvic canal, and fixing the sections.

17. In a pelvic osteotomy procedure wherein an ilial section is rotated and fixed relative to the pelvis to stabilize the coxofemoral joint, the improvement comprising offsetting such ilial section relative to the pelvis to increase the effective width of the pelvic canal, and thereafter fixing the ilial section to the pelvis.

* * * * *